(12) United States Patent
Tsukamoto et al.

(10) Patent No.: US 7,486,048 B2
(45) Date of Patent: Feb. 3, 2009

(54) IMPLANTABLE POWER MODULE FOR POWERING A MEDICAL DEVICE

(75) Inventors: Hisashi Tsukamoto, Saugus, CA (US); Pang Hoo Tan, Newhall, CA (US)

(73) Assignee: Quallion LLC, Sylmar, CA (US)

( * ) Notice: Subject to any disclaimer, the term of this patent is extended or adjusted under 35 U.S.C. 154(b) by 533 days.

(21) Appl. No.: 10/900,883

(22) Filed: Jul. 29, 2004

(65) Prior Publication Data
US 2005/0021100 A1 Jan. 27, 2005

Related U.S. Application Data

(63) Continuation of application No. 10/718,927, filed on Nov. 19, 2003, now Pat. No. 7,009,362, and a continuation of application No. 10/310,390, filed on Dec. 5, 2002, now Pat. No. 6,894,456, and a continuation-in-part of application No. 10/042,898, filed on Jan. 9, 2002, now Pat. No. 6,586,912, and a continuation-in-part of application No. 10/014,757, filed on Nov. 7, 2001, now Pat. No. 6,531,847.

(60) Provisional application No. 60/402,323, filed on Aug. 9, 2002.

(51) Int. Cl.
*H01M 10/44* (2006.01)
*H01M 10/46* (2006.01)
(52) U.S. Cl. ..................................... 320/112
(58) Field of Classification Search ................. 320/103, 320/112, 107, 108, 114, 115; 607/116, 119
See application file for complete search history.

(56) References Cited

U.S. PATENT DOCUMENTS 3,207,631 A 9/1965 Zaromb (Continued)

FOREIGN PATENT DOCUMENTS

EP 0 178 769 A2 4/1986

(Continued)

OTHER PUBLICATIONS

G. MacLean et al., Preliminary Evaulation of Rechargeable Lithium-Ion Cells for an Implantable Battery Pack; 1995, pp. 67-74, vol. 56.

(Continued)

*Primary Examiner*—Edward Tso
(74) *Attorney, Agent, or Firm*—Gaurilovich, Dodd & Lindsey, LLP

(57) ABSTRACT

Disclosed is a medically implantable integrated biocompatible power module incorporating a power source (e.g., battery), a power management circuit (PMC), a magnetically inductive coupling system (MICS) for remote communication and/or inductive charging and a homing device for locating the implanted inductive charging coil. Three configurations are disclosed, each generally suitable for a specified range of energy capacities. The implantable power module (IPM) allows for improved design flexibility for medical devices since the power source may be located remotely and be recharged safely in situ. Special safety aspects may be incorporated, including endothermic phase change heat absorption material (HAM), emergency energy disconnect and emergency energy drain circuits. Communication (one or two way) may be carried out using the inductive charging link, a separate inductive pathway, or other pathway such as RF or via light waves. Homing devices and other means for precisely locating the IPM and/or MICS are disclosed.

64 Claims, 10 Drawing Sheets

U.S. PATENT DOCUMENTS

| | | | |
|---|---|---|---|
| 3,537,907 A | 11/1970 | Wilson | |
| 3,782,814 A | 1/1974 | Greenblatt | |
| 3,794,041 A | 2/1974 | Frei et al. | |
| 3,812,300 A | 5/1974 | Brander et al. | |
| 3,942,535 A | 3/1976 | Schulman | |
| 3,983,336 A | 9/1976 | Malek et al. | |
| 4,010,760 A | 3/1977 | Kraska et al. | |
| 4,022,952 A | 5/1977 | Fritts | |
| 4,075,400 A | 2/1978 | Fritts | |
| 4,119,103 A | 10/1978 | Jirak | |
| 4,197,850 A | 4/1980 | Schulman et al. | |
| 4,207,390 A | 6/1980 | Oehrlein et al. | |
| 4,232,679 A | 11/1980 | Schulman | |
| 4,311,206 A | 1/1982 | Johnson | |
| 4,314,008 A | 2/1982 | Blake | |
| 4,469,104 A | 9/1984 | Peers-Trevarton | |
| 4,495,917 A | 1/1985 | Byers | |
| 4,564,955 A | 1/1986 | Birch et al. | |
| 4,585,089 A | 4/1986 | Topholm | |
| 4,628,907 A | 12/1986 | Epley | |
| 4,232,679 A | 5/1988 | Schulman | |
| 4,741,979 A | 5/1988 | Faust et al. | |
| 4,784,141 A | 11/1988 | Peers-Trevarton | |
| 4,860,750 A | 8/1989 | Frey et al. | |
| 4,972,487 A | 11/1990 | Mangold et al. | |
| 5,025,550 A | 6/1991 | Zirbes et al. | |
| 5,047,044 A | 9/1991 | Smith et al. | |
| 5,084,699 A | 1/1992 | DeMichele | |
| 5,149,603 A | 9/1992 | Fleming et al. | |
| 5,193,540 A | 3/1993 | Schulman et al. | |
| 5,199,893 A | 4/1993 | Fussell | |
| 5,282,858 A | 2/1994 | Bisch et al. | |
| 5,304,214 A * | 4/1994 | DeFord et al. | 607/105 |
| 5,304,915 A | 4/1994 | Sanpei et al. | |
| 5,314,451 A | 5/1994 | Mulier | |
| 5,343,368 A | 8/1994 | Miller | |
| 5,370,669 A | 12/1994 | Daglow et al. | |
| 5,411,537 A | 5/1995 | Munshi et al. | |
| 5,411,538 A | 5/1995 | Lin | |
| 5,478,667 A | 12/1995 | Shackle et al. | |
| 5,535,097 A | 7/1996 | Ruben et al. | |
| 5,573,551 A | 11/1996 | Lin | |
| 5,616,140 A | 4/1997 | Prescott | |
| 5,625,273 A | 4/1997 | Fehling et al. | |
| 5,629,678 A * | 5/1997 | Gargano et al. | 340/573.4 |
| 5,645,960 A | 7/1997 | Scrosati et al. | |
| 5,669,790 A | 9/1997 | Carson et al. | |
| 5,679,026 A | 10/1997 | Fain et al. | |
| 5,684,663 A | 11/1997 | Mitter | |
| 5,702,432 A | 12/1997 | Chen et al. | |
| 5,763,118 A | 6/1998 | Stafford et al. | |
| 5,766,793 A | 6/1998 | Kameishi et al. | |
| 5,814,095 A | 9/1998 | Muller et al. | |
| 5,833,603 A | 11/1998 | Kovacs et al. | |
| H1765 H | 12/1998 | O'Phelan et al. | |
| 5,898,356 A | 4/1999 | Gascoyne et al. | |
| 5,904,646 A | 5/1999 | Jarvik | |
| 5,919,215 A | 7/1999 | Wiklund et al. | |
| 5,951,595 A | 9/1999 | Moberg et al. | |
| 5,989,245 A | 11/1999 | Prescott | |
| 6,006,135 A | 12/1999 | Kast et al. | |
| 6,009,350 A | 12/1999 | Renken | |
| 6,010,800 A | 1/2000 | Stadnick et al. | |
| 6,039,685 A | 3/2000 | Bushek | |
| 6,040,082 A | 3/2000 | Haas et al. | |
| 6,074,774 A | 6/2000 | Semmens et al. | |
| 6,080,188 A | 6/2000 | Rowley et al. | |
| 6,087,809 A | 7/2000 | Gan et al. | |
| 6,102,739 A | 8/2000 | Murakami | |
| 6,120,502 A * | 9/2000 | Michelson | 606/61 |
| 6,127,438 A | 10/2000 | Hasegawa et al. | |
| 6,166,518 A | 12/2000 | Echarri et al. | |
| 6,172,482 B1 | 1/2001 | Eguchi | |
| 6,205,358 B1 | 3/2001 | Haeg et al. | |
| 6,210,824 B1 | 4/2001 | Sullivan et al. | |
| 6,242,893 B1 | 6/2001 | Freedman | |
| 6,252,762 B1 | 6/2001 | Amatucci | |
| 6,259,951 B1 | 7/2001 | Kuzma et al. | |
| 6,268,713 B1 | 7/2001 | Thandiwe | |
| 6,272,382 B1 | 8/2001 | Faltys et al. | |
| 6,273,904 B1 | 8/2001 | Chen et al. | |
| 6,278,258 B1 * | 8/2001 | Echarri et al. | 320/130 |
| 6,287,136 B1 | 9/2001 | Deutsch | |
| 6,308,101 B1 | 10/2001 | Faltys et al. | |
| 6,315,721 B2 | 11/2001 | Schulman et al. | |
| 6,327,502 B1 | 12/2001 | Johansson et al. | |
| 6,358,281 B1 * | 3/2002 | Berrang et al. | 623/10 |
| 6,400,991 B1 | 6/2002 | Kung | |
| 6,426,628 B1 * | 7/2002 | Palm et al. | 324/427 |
| 6,453,198 B1 | 9/2002 | Torgerson et al. | |
| 6,553,263 B1 | 4/2003 | Meadows et al. | |
| 6,564,807 B1 | 5/2003 | Schulman et al. | |
| 6,586,912 B1 | 7/2003 | Tsukamoto et al. | |
| 6,596,433 B2 | 7/2003 | Gudmundsson et al. | |
| 6,627,344 B2 | 9/2003 | Kang et al. | |
| 6,748,094 B1 | 6/2004 | Tziviskos et al. | |
| 2001/0016289 A1 | 8/2001 | Oura et al. | |
| 2001/0031909 A1 | 10/2001 | Faltys et al. | |
| 2002/0019669 A1 | 2/2002 | Berrang et al. | |
| 2002/0098410 A1 | 7/2002 | Leysieffer et al. | |
| 2004/0004464 A1 | 1/2004 | Tsukamoto et al. | |

FOREIGN PATENT DOCUMENTS

| | | |
|---|---|---|
| EP | 0 178 769 B1 | 4/1986 |
| EP | 0 806 806 A1 | 11/1997 |
| EP | 0 805 806 B1 | 1/2002 |
| JP | 55-111060 A2 | 6/1980 |
| JP | 55-119346 A2 | 9/1980 |
| JP | 55-119347 A2 | 9/1980 |
| JP | 56-028463 A2 | 3/1981 |
| JP | 56-152474 A2 | 12/1981 |
| JP | 56-162473 A2 | 12/1981 |
| JP | 57-072272 A2 | 5/1982 |
| JP | 57-138774 A2 | 8/1982 |
| JP | 58-063666 A2 | 10/1982 |
| JP | 58-082482 A2 | 5/1983 |
| JP | 58-097255 A2 | 6/1983 |
| JP | 58-129652 A2 | 6/1983 |
| JP | 58-209059 A2 | 12/1983 |
| JP | 59-090353 A2 | 5/1984 |
| JP | 59-128774 A2 | 7/1984 |
| JP | 60-025157 A2 | 2/1985 |
| JP | 60-068552 | 4/1985 |
| JP | 60-077350 A2 | 5/1985 |
| JP | 60-138847 | 7/1985 |
| JP | 61-147473 A2 | 7/1986 |
| JP | 61-114466 | 8/1986 |
| JP | 62-139245 | 6/1987 |
| JP | 62-154555 A2 | 7/1987 |
| JP | 01-140558 A2 | 6/1989 |
| JP | 02-064861 A2 | 2/1990 |
| JP | 02-075152 A2 | 3/1990 |
| JP | 02-148577 A2 | 6/1990 |
| JP | 04-206339 A2 | 11/1990 |
| JP | 03-263753 A2 | 11/1991 |
| JP | 05-101731 | 4/1993 |
| JP | 06-114036 A2 | 4/1994 |
| JP | 07-029563 A2 | 1/1995 |
| JP | 07-057719 | 3/1995 |
| JP | 07-094189 A2 | 4/1995 |
| JP | 07-130347 A2 | 5/1995 |
| JP | 07-130349 A2 | 5/1995 |
| JP | 07-240198 | 9/1995 |

| | | | |
|---|---|---|---|
| JP | 07-272702 A2 | 10/1995 |
| JP | 07-272708 | 10/1995 |
| JP | 07-272717 A2 | 10/1995 |
| JP | 08-106886 A2 | 4/1996 |
| JP | 08-241708 A2 | 9/1996 |
| JP | 09-237615 | 9/1997 |
| JP | 09-237618 A2 | 9/1997 |
| JP | 09-327447 A2 | 12/1997 |
| JP | 10-031997 A2 | 2/1998 |
| JP | 10-050348 A2 | 2/1998 |
| JP | 10-064548 A2 | 3/1998 |
| JP | 10-084549 A2 | 3/1998 |
| JP | 08-138835 A2 | 5/1998 |
| JP | 10-139918 A2 | 5/1998 |
| JP | 10-279717 A2 | 10/1998 |
| JP | 11-069497 | 3/1999 |
| JP | 11-204151 A2 | 7/1999 |
| JP | 11-238518 A2 | 8/1999 |
| JP | 11-240970 A2 | 9/1999 |
| JP | 11-268118 A2 | 10/1999 |
| JP | 11-307081 A2 | 11/1999 |
| JP | 2000-100460 A2 | 4/2000 |
| JP | 2000-285873 A2 | 10/2000 |
| JP | 2001-043893 A2 | 2/2001 |
| JP | 2001-06486 A2 | 3/2001 |
| JP | 2001-060468 A2 | 3/2001 |
| JP | 2001-307688 A2 | 11/2001 |
| WO | WO 00/79625 A1 | 12/2000 |
| WO | WO 01/08578 A1 | 2/2001 |
| WO | WO 02/07598 A1 | 1/2002 |
| WO | WO 02/41755 A2 | 5/2002 |
| WO | WO 03/041208 A1 | 5/2003 |
| WO | WO 03/061032 A2 | 7/2003 |
| WO | WO 03/061032 A3 | 7/2003 |
| WO | WO 2004/014214 A1 | 2/2004 |
| WO | WO 2004-014214 A2 | 2/2004 |

OTHER PUBLICATIONS

Light Sciences Corporation web pages, www.lightsci.com, no date.
R. Matthews, Instant Imaging Device Gives GPs Safe New Window into the Body, website: http://www.telegraph.co.uk/connected/main.jhtml?xml=/connected/2002/10/09/ecnxray06.xml, no date.
International Search Report, PCT/US03/24168, International Filing Date Jul. 31, 2003; Mailing Date of Report Mar. 3, 2004.

* cited by examiner

IMPLANTABLE POWER MODULE FOR POWERING A MEDICAL DEVICE

REFERENCE TO PRIOR FILED APPLICATIONS

This application is a continuation of U.S. patent application Ser. No. 10/718,927, filed Nov. 19, 2003 now U.S. Pat. No. 7,009,362, and a continuation of allowed U.S. patent application Ser. No. 10/310,390 filed Dec. 5. 2002 now U.S. Pat. No. 6,894,456, which claims priority to provisional application No. 60/402,323 filed Aug. 9, 2002 and is a continuation-in-part of application Ser. No. 10/042,898 filed Jan. 9, 2002 entitled "Method and Apparatus for Amplitude Limiting Battery Temperature Spikes", now U.S. Pat. No. 6,586,912, and application Ser. No. 10/014,757 filed Nov. 7, 2001 entitled "Electrochemical Battery Safety Method, Device and System", now U.S. Pat. No. 6,531,847, each of which is incorporated herein in its entirety by reference, including all disclosures submitted therewith.

GOVERNMENT LICENSE RIGHTS

None

FIELD

The present invention relates to medically implanted biocompatible power modules. More particularly, the present invention relates to integrated modules incorporating a power source (e.g. battery), a power management circuit (hereinafter "PMC"), and a magnetically inductive coupling system (hereinafter "MICS") for transcutaneous charging and remote communication. The present invention also relates to homing devices for medically implanted apparatus.

BACKGROUND

The use of implanted medical devices is becoming increasingly important in the treatment of diseases and disabilities. Such devices include, but are not limited to, implantable cardiac defibrillators (see e.g., U.S. Pat. No. 5,817,130 to Cox et al., U.S. Pat. Nos. 6,427,083 and 6,418,342 both to Owen, et al.), cardiac pacemakers (see e.g., U.S. Pat. No. 6,421,564 to Yerich, et al. and U.S. Pat. 5,411,537 to Munshi et al., hereinafter the '537 patent), cardiac assist pumps (see e.g., U.S. Pat. Nos. 6,387,037 and 6,299,575 both to Bolling, U.S. Pat Nos. 6,336,939 and 6,346,120 both to Yamazaki, Tevaearai et al., *Performance of a New Implantable Cardiac Assist Centrifugal Pump,* International Society for Artificial Organs, February 2000 <http://www.cardiacassist.com/research/articles/ASAIO01.pdf>, artificial hearts (see e.g., U.S. Pat. No. 6,346,120 to Yamazaki, et al.), neuromuscular stimulators (see e.g., U.S. Pat. No. 6,163,725 to Peckham, et al.), cochlear implants (see e.g., U.S. Pat. No. 5,344,387 to Lupin, artificial hearing and vision devices (see e.g., U.S. Pat. No. 6,394,947 to Leysieffer (hearing) and U.S. Pat. No. 5,556,423 to Chow, et al. (vision)), deep brain stimulation devices (see e.g., U.S. Pat. No. 6,427,086 to Fischell, et al.), electronic pain blockers, automatic drug delivery (see e.g., U.S. Pat. No. 6,416,493 to Del Giglio), therapeutic alarms/signals (see e.g., U.S. Pat. No. 6,328,699 to Eigler, et al.) and sensor/biotelemetry devices (see e.g., U.S. Pat. No. 6,424,867 to Snell, et al. and U.S. Pat. No. 6,409,674 to Brockway, et al.). As a result, people are experiencing longer and much improved qualities of life. New and more sophisticated bioelectronic devices continue to be developed and it is anticipated that the need for better sources of power will increase, with a growing need for implantable power modules with improved reliability, safety and cost-effectiveness. The present invention results from extensive research and development in the area of implantable electrical power sources, particularly rechargeable batteries and their associated devices.

Numerous electrically powered medical devices have been implanted in recent years. Power to operate these devices has been provided from an external source or, if implanted, a power source has been specifically designed for each particular device.

The need for a standardized power source around which a wide variety of medical devices may be designed, and one which is rechargeable by transcutaneous induction has to date not been met. Moreover, such a power module could be located remotely from a medical device (e.g., an atrial assist pump), minimizing stress on the patient by placing it in a more spacious body cavity (e.g., a subcutaneous pocket created in the abdomen). Such an integrated power source would give significantly increased design flexibility to designers of implantable medical devices. The present invention overcomes the limitations inherent in having to provide external power, external recharging connections, or surgically-replaceable primary batteries for implantable medical devices. Moreover, it overcomes the limitations of other implantable batteries with inductively charged batteries, allowing broad flexibility for design of implantable medical devices. In addition, the present invention overcomes the difficulties associated with precisely locating the implanted secondary charging coil to maximize charging efficiency.

A primary objective of the present invention is to provide an implantable power module (hereinafter "IPM") containing an energy storage device (e.g., a battery), a PMC, and an MICS for remote communication.

A further objective of the invention is to provide an IPM with one or more homing devices or internal functions for easily locating the device once implanted for possible explant, medical treatment, or recharging purposes.

A further objective of the invention is to provide an IPM incorporating safety devices and design aspects to prevent overheating in the event of a malfunction such as an internal or external short circuit, overcharging, overdischarging, or breach of the battery case.

Yet a further objective of the invention is to provide an EPM that allows inductive recharging of the energy storage device without excessive inductive heating of any portion of the EPM or associated medical devices.

A further objective of the invention is to provide a means for precisely locating a secondary charging coil, or any other implanted device.

SUMMARY

The present invention comprises an IPM which can be implanted in a human or animal for extended periods of time, and, contained within a hermetic biocompatible case having a highly reliable external connector (external hermetic plug), a source of electrical power, a control circuit, an inductive recharging coil (in the case of secondary batteries and/or capacitors), a homing device for precisely locating the implanted module, and safety devices and design aspects to protect the patient in which the IPM is implanted. The source of power may be one or more primary or secondary cells (hereinafter, "battery"), a capacitor, a nuclear-heated thermopile or nuclear battery, or combinations of the above. Lithium cells are generally considered the best overall compromise of energy capacity, reliability, safety, and rate capability. However, hybrid devices having properties of both lithium cells and super capacitors may have improved performance depending on the demands of the device it is powering. While the term "battery" is used for convenience herein, its meaning may include any electrical storage or generation device.

The present invention has numerous advantages over prior art. (1) It provides design flexibility for medical device developers who do not need to restrict their designs in order to accommodate a power supply. (2) The invention provides a stand-alone power source that can be readily connected to a medical device or multiple devices with a sealed connection within the body. (3) The invention can be located remotely from the medical device it is powering, allowing implantation of medical devices in confined spaces, connecting to the IPM via power leads run within the body. (4) In its smaller embodiments, the present invention can be injected or laparoscopically inserted, reducing the intrusiveness, trauma and cost of surgical procedures, and reducing recovery time. (5) The invention may be located readily for surgical intervention, replacement, etc. (6) The patient is protected from potentially catastrophic failures of the power source by several active and passive design features. (7) The implanted charging coil, or the IPM itself, can be located with great precision.

The IPM can be designed in several general configurations, primarily dictated by size or capacity.

DETAILED DESCRIPTION

Figure 1A:
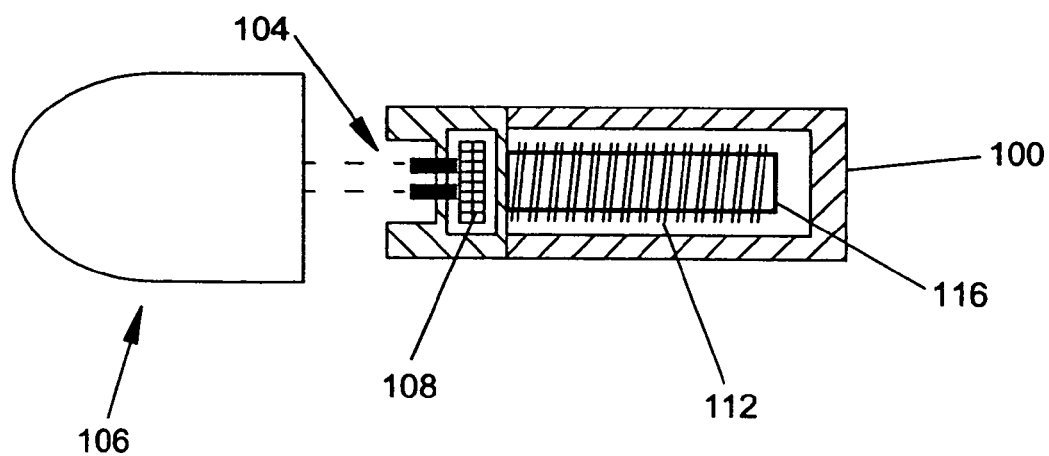
FIG. 1a is a cross-sectional diagram of a preferred embodiment of the present invention.
Figure 1B:
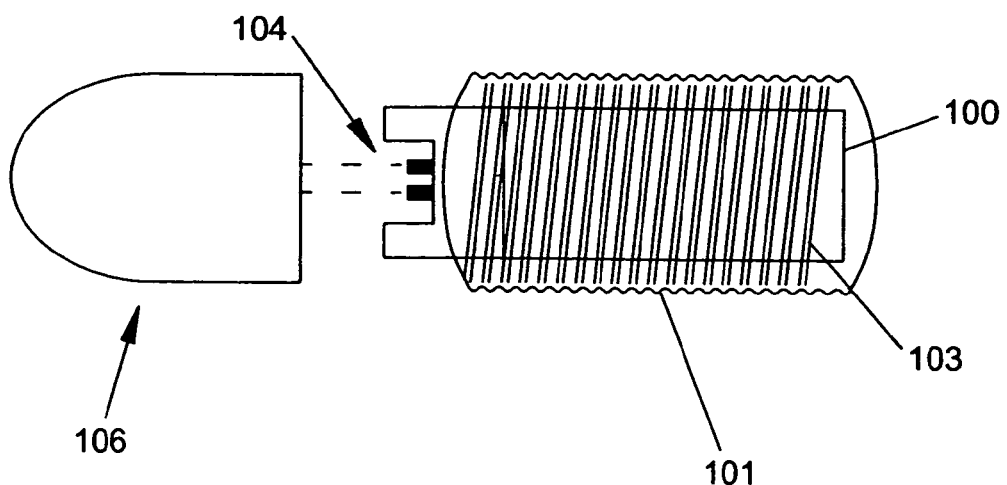
FIG. 1b is a cross-sectional diagram of another preferred embodiment of the present invention.

Referring to FIG. 1a, the IPM of the present invention is a standalone, biocompatible power device with the following key components: a hermetic biocompatible case 100, a highly reliable external connector (i.e., an external hermetic plug) 104 for providing power to a medical device 106, a PMC 108, and a MICS 112 for remote communication. Alternative communications couples using sound or electromagnetic energy such as a radio frequency (RF) receiver, light signal receiver and the like may be substituted for the MICS 112 for the purpose of communicating with the IPM. The connector 104 is designed for easy and secure (but removable) connection of the IPM to the implantable medical device 106. The PMC 108 is a data processing circuit also incorporating a homing function to assist in locating the IPM after it is implanted. The homing function may be provided by a passive transponder, a magnet, an RF transmitter, a radioactive element, a light-producing device (e.g., an LED in the visible spectrum or UV to near infrared), or a metal component that can be detected with a metal detector (such as one using magnetic flux variation. See e.g., U.S. Pat. No. 5,057,095 to Fabian). In addition, the IPM contains a power source 116, in this example a secondary lithium cell. The MICS 112 charges the power source 116 by producing a current as the result of a fluctuating magnetic field being imposed upon the MICS 112. The hermetic case 100 is constructed of biocompatible materials that have low magnetic interference properties such as ceramic and/or titanium or titanium alloy. The case may be neutral, or may be positively or negatively charged. As shown in FIG. 1b, the coil 103 of the MICS may be located outside case 100 and coated with a polymer coating 101, thus avoiding energy absorption by the case. The power source 116 is coated with ferrite or other ferrous material to shield, and thus minimize heating of the power source during inductive charging. It has been discovered that precise location of the implanted secondary coil is critical to efficient charging and communication. Therefore, the use of a homing device is much preferred over using current maximization in the primary coil as described in the '537 patent. This approach is inexact and results in significant loss of charging efficiency. Tests have shown an error as small as 0.5 cm results in a charging current drop of about 80%, depending on the power of the primary and secondary coils. The use of a precise homing device is therefore much preferred.

PREFERRED EMBODIMENT

Figure 2A:
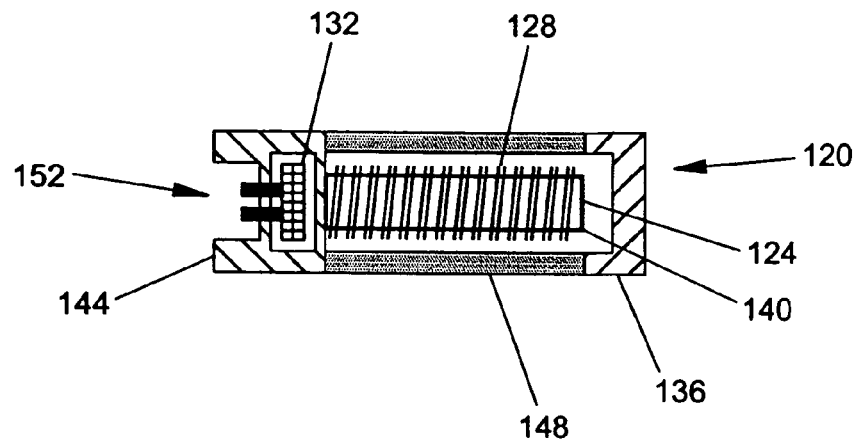
FIGS. 2a, 2b, 2c, 2d and 2e are cross sectional diagrams of alternative configurations of the preferred embodiment of the present invention.
Figure 2B:
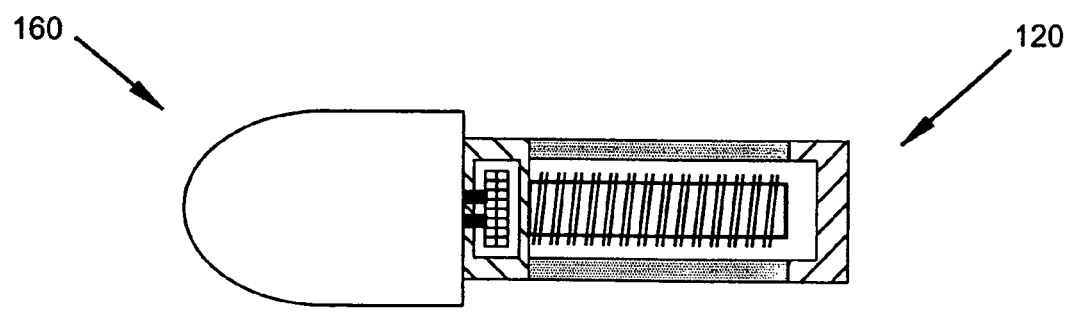

FIGS. 2a, 2b, 2c and 2d illustrate the general configurations in which the present invention can be manufactured. FIGS. 2a and 2b illustrate the configuration of the IPM 120 for the smallest range, approximately 0.1-10 mAh. With reference to FIG. 2a, in this monolithic configuration, a rechargeable battery 124, a secondary magnetic inductive coil 128, and a PMC 132 are all housed within a biocompatible housing 136. The battery may be any geometry, cylindrical or prismatic, and is coated with a ferrite material 140 to shield, and thus protect it from being heated when it is being inductively charged. This also increases the efficiency of inductive charging since the field is not lost interacting with the battery casing. Further, shielding the battery with ferrite material permits the secondary inductive charging coil 128 to be located in close proximity to the battery 124, even wrapped around it to save space. When wrapped around the battery, the coil 128 may be wrapped around either axis. This arrangement allows the battery to be implanted relatively deep within the tissue mass without significant performance loss. A ferrite shield may also take the form of a flat plate or wall (not shown) interposed between the charging coil 128 and the battery 124.

The PMC 132 provides functions for managing the safety and operation of the IPM 120. This includes shutdown features such as overcharging, over-discharging, thermal sensory feedback, charge/voltage controls, and a homing function. The homing function (more fully describe below) allows the IPM 120 to be easily located for future intervention.

The biocompatible housing 136 is made of titanium or a titanium alloy 144, ceramic 148, other biocompatible metal alloy, or a combination of metal and ceramic (as illustrated here). Ceramic 148 is the preferred housing material since it has infinite electrical resistance and hence is transparent to a magnetic field, minimizing interference, and facilitating more efficient inductive charging. The external case 136 also incorporates an external connection feature 152 to which one or more devices (not shown) can be connected.

Figure 2C:
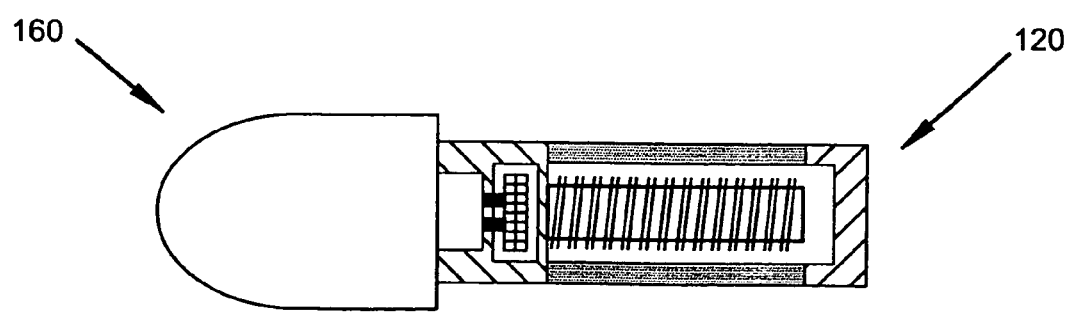

FIGS. 2b and 2c illustrate two alternative connector geometries for the device illustrated in FIG. 2a. Here, a medical device 160 is plugged directly into this relatively small IPM. In FIG. 2b, the connector of the medical device 160 fully surrounds one end of the IPM, creating a hermetic seal. In FIG. 2c, the medical device 160 inserts into a cavity of the IPM also hermetically sealing the connection. Many other connector geometries which are insubstantially different, are equally applicable and will be well understood by those of ordinary skill in the art.

Figure 2D:
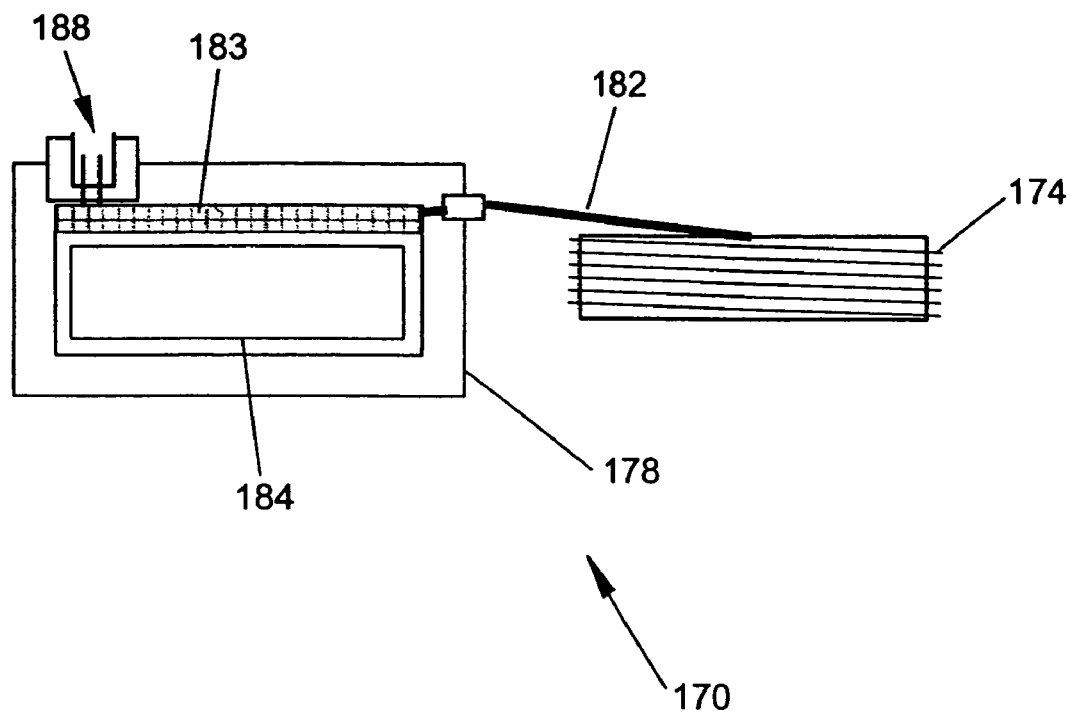

FIG. 2d illustrates the configuration of the IPM 170 more suited for the middle range of approximately 10-500 mAh. This size range IPM generally has all the characteristics of the smaller unit described above with reference to FIGS. 2a and 2b. However, the secondary inductive charging coil 174 may be placed in a separate submodule external to the IPM casing 178 and is connected via a lead 182 to the PMC 183 which controls the charging of the battery 184. This allows the secondary coil to be implanted at strategic locations inside the body that may not otherwise be possible if the coil were contained within the IPM. This also reduces interference with charging and external communication with the IPM. In this configuration, the IPM may be connected directly to medical devices or be located remotely and be connected with leads (not shown) via a highly reliable hermetic connector 188.

Figure 2E:
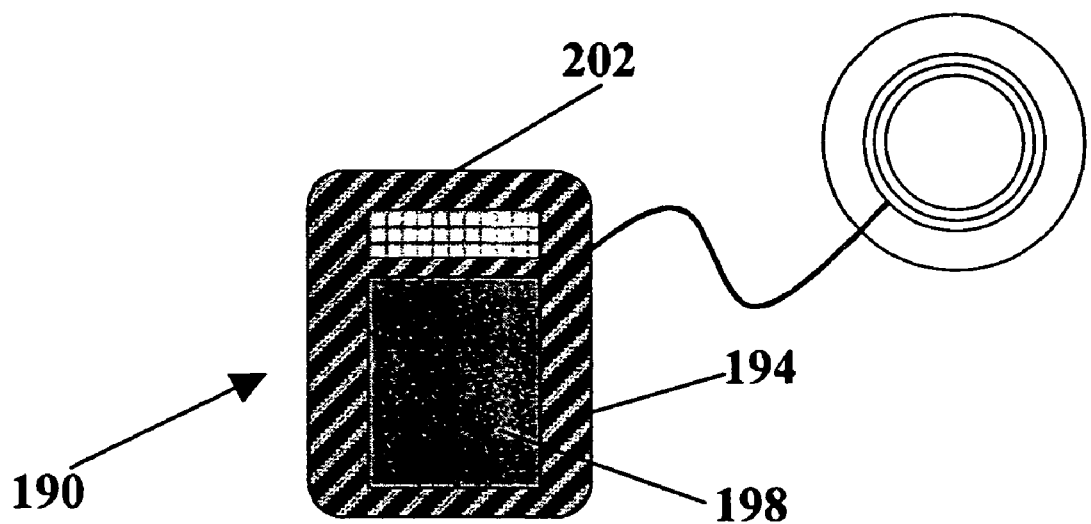

FIG. 2e illustrates the largest size design configuration, generally applicable to approximately 500 mAh to 20 Ah. This size IPM 190 incorporates all of the attributes of the middle size IPM described above with reference to FIG. 2c. However, in this capacity range, safety and biomechanical compatibility are of even greater importance. Therefore, special design aspects are included. Of particular concern is potential overheating in the event of a battery failure such as an internal or external short circuit. Therefore, heat absorption material ("HAM") 194 may be provided. HAM preferably takes the form of paraffin or other material with an endothermic melting phase change at about between 42° C. to 80° C. The HAM surrounds and has intimate contact with the external surface of the battery 198, and is encapsulated in the biocompatible case 202. The HAM may be incorporated into the battery (i.e., enclosed within the battery case), or located external to the battery. When located internally, the HAM must be electrochemically compatible with the battery chemistry. Alternatively or in addition, other heat protective means such as thermal insulation or heat sink can be provided.

Figure 3A:
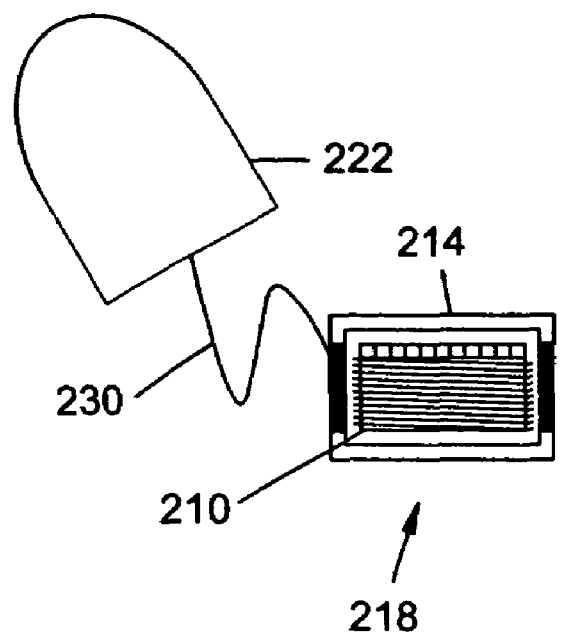
FIGS. 3a and 3b are diagrams of two configurations of a middle-size (approximately 10-500 mAh) IPM.
Figure 3B:
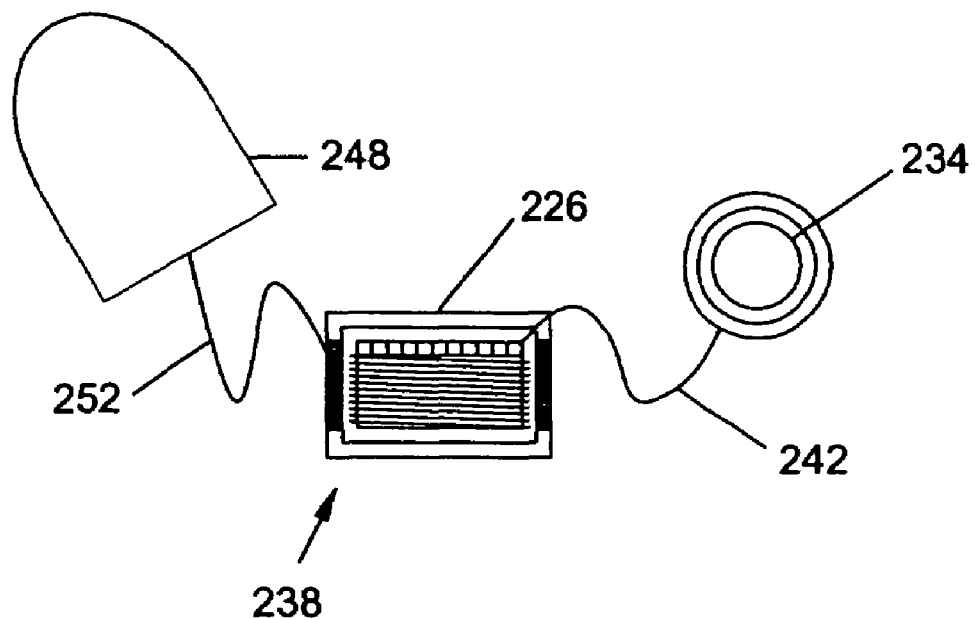

FIGS. 3a and 3b illustrate middle size (10-500 mAh) IPM configurations in which the secondary inductive charging coil is located with the IPM case (FIG. 3a) or remotely (FIG. 3b). In FIG. 3a, coil 210 is provided for inductive charging and optionally data communication, and surrounds the battery located within the hermetic case 214 of the IPM 218. Alternatively, coil 210 may be located within case 214 but not surround the battery. The medical device 222 is located remotely outside of the hermetic case 214 and connected with a lead 230. Note that at least a portion of case 214 is shown as ceramic for the reasons discussed above; this also saves space by obviating the need for insulation between the coil and case. In FIG. 3b the secondary inductive charging coil 234 is located remote to the IPM case 226 and connected with a lead 242. The medical device 248 powered by the IPM 238 is located remotely and connected for power and communication by a lead 252. Coil 234 may also be used for data communication, such as to convey battery status. Alternatively, optional coil 210 may be provided for data communication, such as to convey battery status or location to an external device, and may surround the battery, as shown, or may be located within case 214 but not surround the battery.

Figure 4:
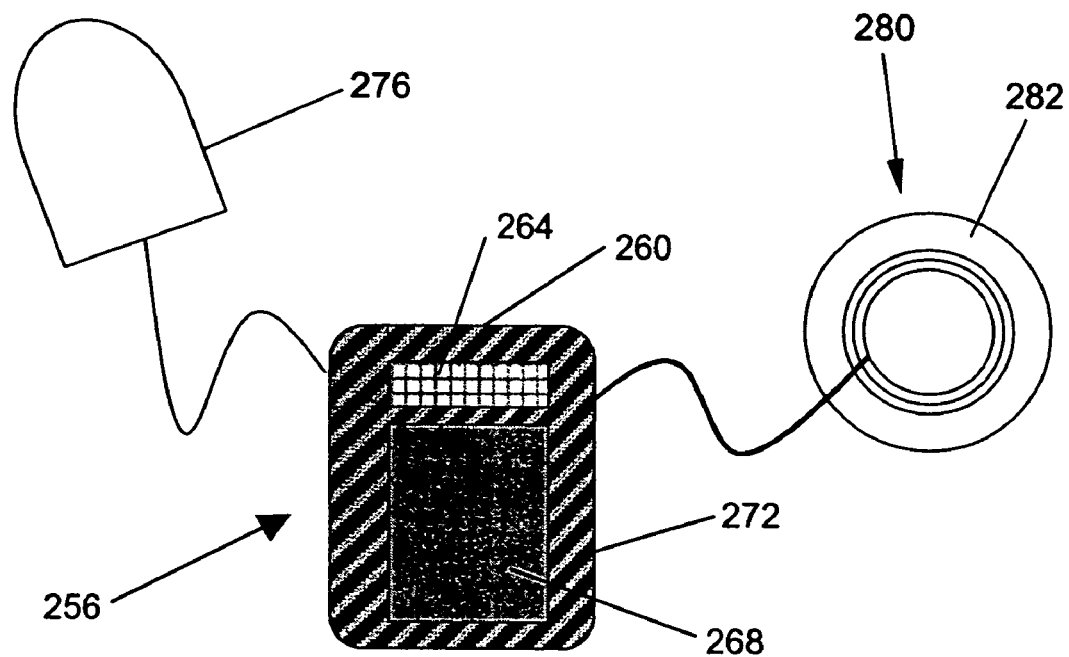
FIG. 4 is a schematic/cross-sectional diagram of a large-size (approximately 500 mAh to 20 Ah) IPM.

FIG. 4 more fully illustrates the large size (500 mAh-20 Ah) configuration of the IPM 256. Here, the hermetic biocompatible case 260 encloses the PMC 264 and battery 268. The battery is surrounded by HAM 272 which will melt and absorb the heat generated by the battery in the event of overheating (e.g., from an internal or external short circuit or overcharging). An alternative embodiment would be to place the HAM within the battery 268. The PMC 264 senses several parameters and controls the flow of electricity to the medical device 276. In the event of a fault (e.g., internal short, overheating, overcharging or overdischarging) the PMC 264 will disconnect the power to the medical device 276 or from inductive charging coil 280. An additional feature that can be incorporated is an emergency energy drain in which, if the PMC senses a short circuit (particularly an internal short), it will connect the terminals of battery directly to the secondary inductive charging coil, or other low resistance circuit or device, to rapidly deplete the energy content of the battery. Tests have shown that such action, if carried out rapidly, will significantly reduce the peak temperature of a shorted battery, minimizing the possibility of a breach of its case. If used as an emergency energy drain ("energy dump"), the-secondary inductive coil may be encapsulated in HAM 282.

The PMC 264 also controls the rate of charge from the inductive charging coil 280. Additionally, the PMC 264 incorporates a precise homing function to assist in easily locating the IPM. The PMC may also incorporate a communication means for remotely interrogating the status of the IPM, switching it on or off, programming it or otherwise adjusting its performance, or alerting a remote receiver of a malfunction or abnormal state. Such communications feature will normally take the form of signals carried on the inductive charging pathway (e.g., pulses or modulation of the inductive field) or radio frequency transmissions, but may also be light signals (visible or invisible spectrum; 400 to 700 nm or 0.8 to 2.5-μm ranges), aural, tactile (e.g., piezoelectric device), chemical (e.g., the release of a taste to alert the patient of a malfunction) or a low-level radioactive source. An initiator circuit (not shown) may be included which, when signaled would switch on an RF transmitter (not shown) located at the center of the secondary charging coil 280 to assist in precisely finding its location. A less desirable means for locating the charging coil 280 would be the use of a biocompatible tendril or protrusion (not shown) extending from a known location on the charging coil 280 (e.g., the center) to near the top layer of skin (intercutaneously) so that it can be felt by touch or mild palpation. Extending the tendril or protrusion through the skin (transcutaneously) is less preferred due to the increased risk of infection, but may be used where warranted.

The external surface of the case has soft contours to avoid biostress, which is a typical human body reaction to foreign objects with sharp edges.

Figure 5:
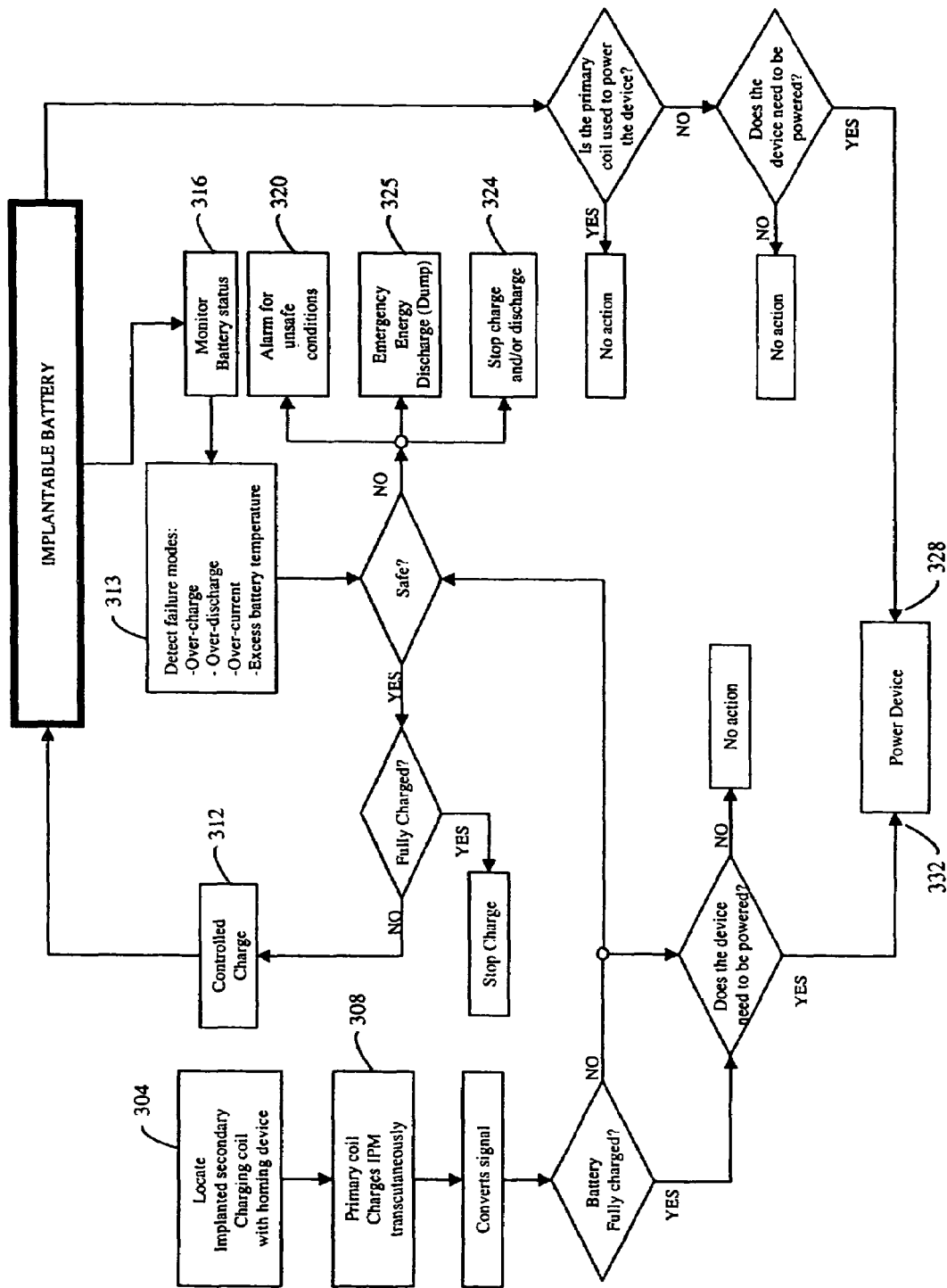
FIG. 5 is an operational logic flow diagram for the IPM.

FIG. 5 is an operational logic flow diagram for the IPM, which is helpful in understanding the basic functions of the present invention. After the IPM is implanted in a patient, the implanted charging coil is located using a homing device 304. The homing device may be as simple as a metal detector, implanted magnet, or implanted passive transponder. Alternatively, the homing device may incorporate an RF transmitter. Once located, a primary inductive coil is placed as precisely as possible in close proximity to the implanted secondary charging coil, and an inductive alternating current or pulsed DC field is initiated in the primary coil to inductively charge the IPM transcutaneously 308. During the charging, the Charging Circuit continuously senses voltage and/or current flowing to the implanted battery, and, if it detects the battery is less than fully charged, provides charging (current) to the implanted battery 312. At all times, the Protection Circuit monitors the IPM 316, including the battery and detects abnormal states such as Over-Charge, Over-Discharge, Over-Current, and Excess Battery Temperature 313. If it detects an abnormal and unsafe parameter, the Protection Circuit can reduce or stop the flow of current to the battery 324, or rapidly discharge the entire energy content of the battery to a low resistance emergency energy drain (dump) 325. Tests carried out demonstrate that the temperature of a fully-charged 320 mAh lithium ion cell following a sudden nail penetration (simulating an internal fault) will rise to about 118° C. with no emergency energy dump circuit, but to only 90° C. if the terminals are subsequently, rapidly connected across a 0.008 ohm wire (energy dump). Emergency energy drain systems for larger batteries placed in situ may utilize heat absorption and protection components such as HAM encased in thermally insulated or low conductivity cases. As discussed above, the secondary charging coil may be used as the energy drain and may be encapsulated in HAM.

Additionally, the Protection Circuit communicates with the outside world providing battery status and alarms for unsafe conditions (e.g., low battery, over voltage, excess heat) 320. Based on the monitored parameters, the protection circuit enables or disables charging or discharging of the battery 324 (to the device). If enabled, the device receives current from the battery 328 and/or the primary coil 332. Additional functions may also be included such as primary or back-up control circuitry for the implanted device, biotelemetry, and other diagnostic functions. Optionally, the system may be controlled from outside the patient via an External Control Function (not shown). A receiver may be incorporated into the Protection Circuit, or may be incorporated as a separate or hybrid circuit. However incorporated, the receiver functions to respond to signals from outside the patient to modify the function of the IPM or the implanted medical device.

Figure 6:
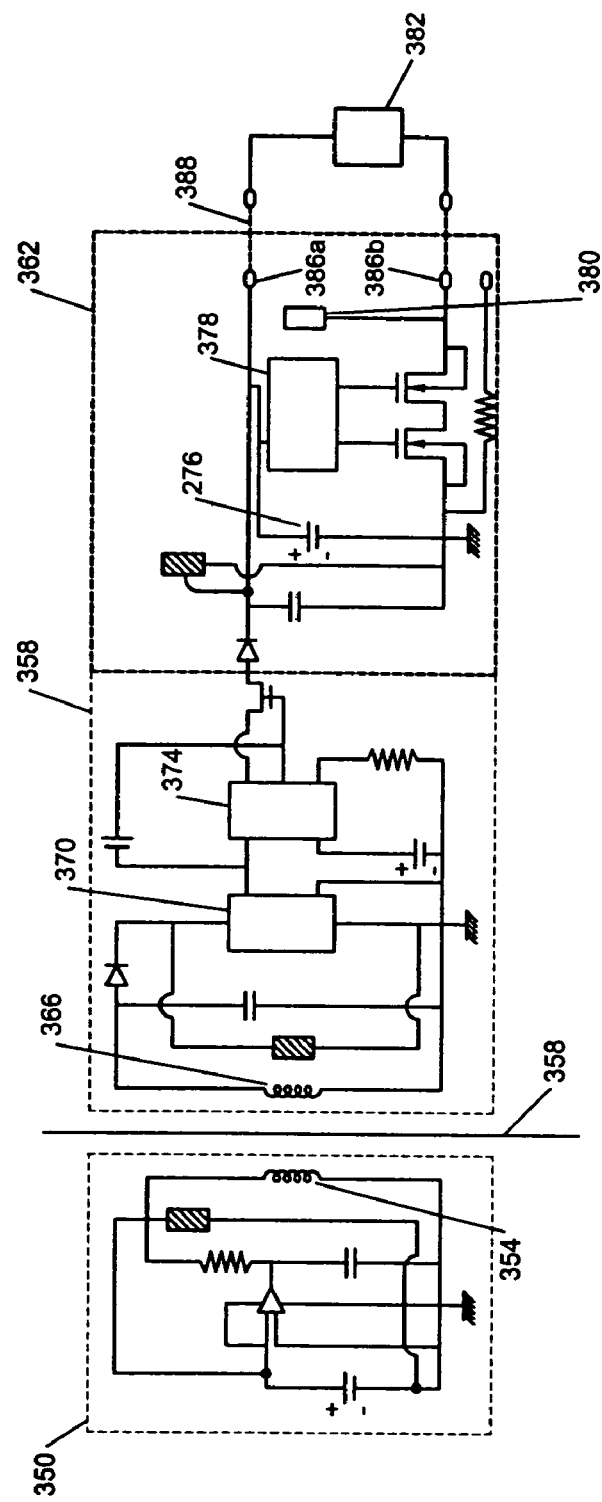
FIG. 6 is an electrical schematic diagram of an IPM.

FIG. 6 is an electrical schematic diagram of an IPM. Shown is an external charger having a primary induction coil C1 354 for charging the IPM through the patient's skin 358. The implanted portion includes the Internal Charger Circuit 358 and the Protection Circuit 362. The Internal Charger Circuit 358 contains the secondary charger coil and two integrated circuits 370 (IC1) and 374 (IC2). IC1 370 steps up or down the input DC voltage to the correct voltage for charging. IC2 374 conducts the charging current to the battery 276 through the Protection Circuit 362. The Protection Circuit 362 contains an integrated circuit 378 (IC3), which functions to protect the battery 276 from under- or over-charge, abnormal current, and/or abnormal load. If all conditions are within normal ranges, current is provided to the implanted medical device 382 such as a left ventricular assist device, artificial heart, artificial vision unit, etc. The implanted medical device 382 is connected to the IPM via highly reliable connectors 386a and 386b. The connectors would normally combine both power and data communication functions. The implanted medical device 382 may be located remotely from the IPM and connected with leads 388 that are routed through the patient's tissue. The design of the charging and protection circuit may further include remote communication via the inductive charging link using the secondary charging coil 366 or an alternate link (e.g., RF) 380 to communicate status and conditions to an external device. Normally the charging circuit 358 will be located together with the Protection Circuit 362, although they may be separated as separate modules if space or other considerations require it. The monitoring and control circuitry is well known to those skilled in the art of rechargeable batteries and related circuits, specifically with regard to battery protection (under/over charge and over heat protection). Therefore, FIG. 6 will be understood by those skilled in the art and many variations of the specific design may be implemented without departure from the claimed invention. Communications circuitry may be added to the circuitry to enable remote monitoring of the function and state of the components of the system, or to initiate changes to the function of the IPM and/or the implanted medical device 382. Similarly, a homing device to locate the secondary inductive charging coil will normally be added to assist in locating the implanted secondary charging coil for charging and/or communication. Monitoring and/or control circuitry specific to the implanted medical device may be incorporated in the IPM where it is advantageous to save space or provide redundancy. In addition, circuitry may be combined into a single data processing circuit (chip) as is well understood in the art.

Figure 7:
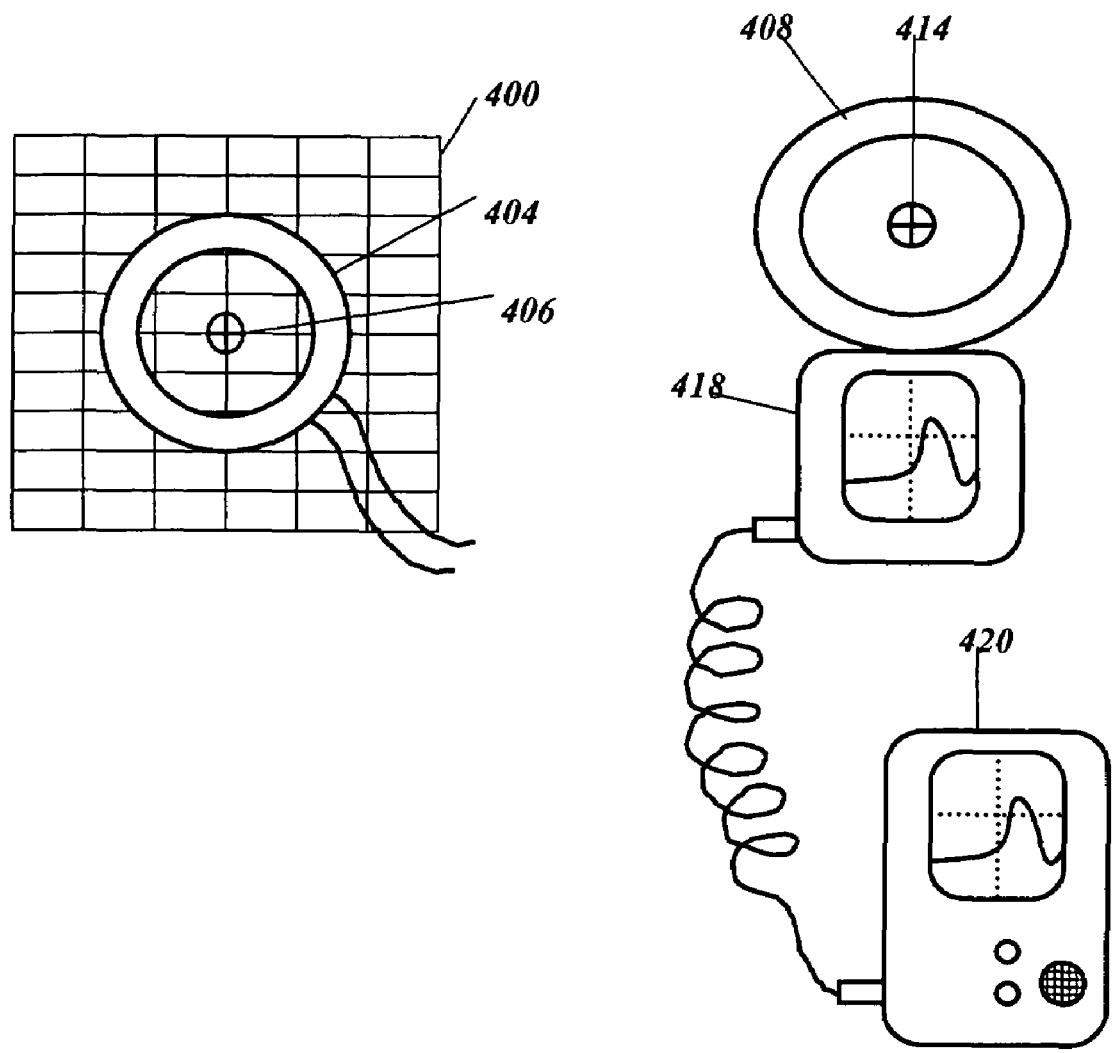
FIG. 7 is a diagram of a homing device using a linear output sensor or Hall effect sensor.

FIG. 7 illustrates the use of implanted magnetic material and a Hall effect sensor for precisely locating the secondary coil. Here, a layer of magnetic material 400 is placed directly under the secondary charging coil 404. The magnetic material 400 is made in such a way that the highest or lowest magnetic strength is in the exact center 406 and located in the center of the secondary coil 404. Fabricating such a layer of magnetic material is well known in the art. The primary charger coil 408 incorporates a linear output sensor or Hall effect sensor 414 at its center point. The sensor 414 is interoperatively connected to a sensor circuit 418, which provides feedback to the user, indicating the highest or lowest magnetic flux when the primary charger coil 408 is precisely located at the center of the secondary charging coil 404. Feedback to the user may be in the form of a visual signal (e.g., dynamic graph, progressive lights, etc.) and/or audible signal device 418 to indicate the relative position of the primary charger coil 408 to the secondary charging coil 404 and when it is properly aligned for the most efficient inductive charging. The preferred embodiment would use maximum magnetic field in the center of the secondary charging coil 404 and a display located directly on the primary coil unit 408. However, the display and/or an audible signal device may be remotely located on a remote unit 420 communicating with the primary charging coil unit either by direct connection or by telemetric connection (RF, IR, etc.).

Figure 8:
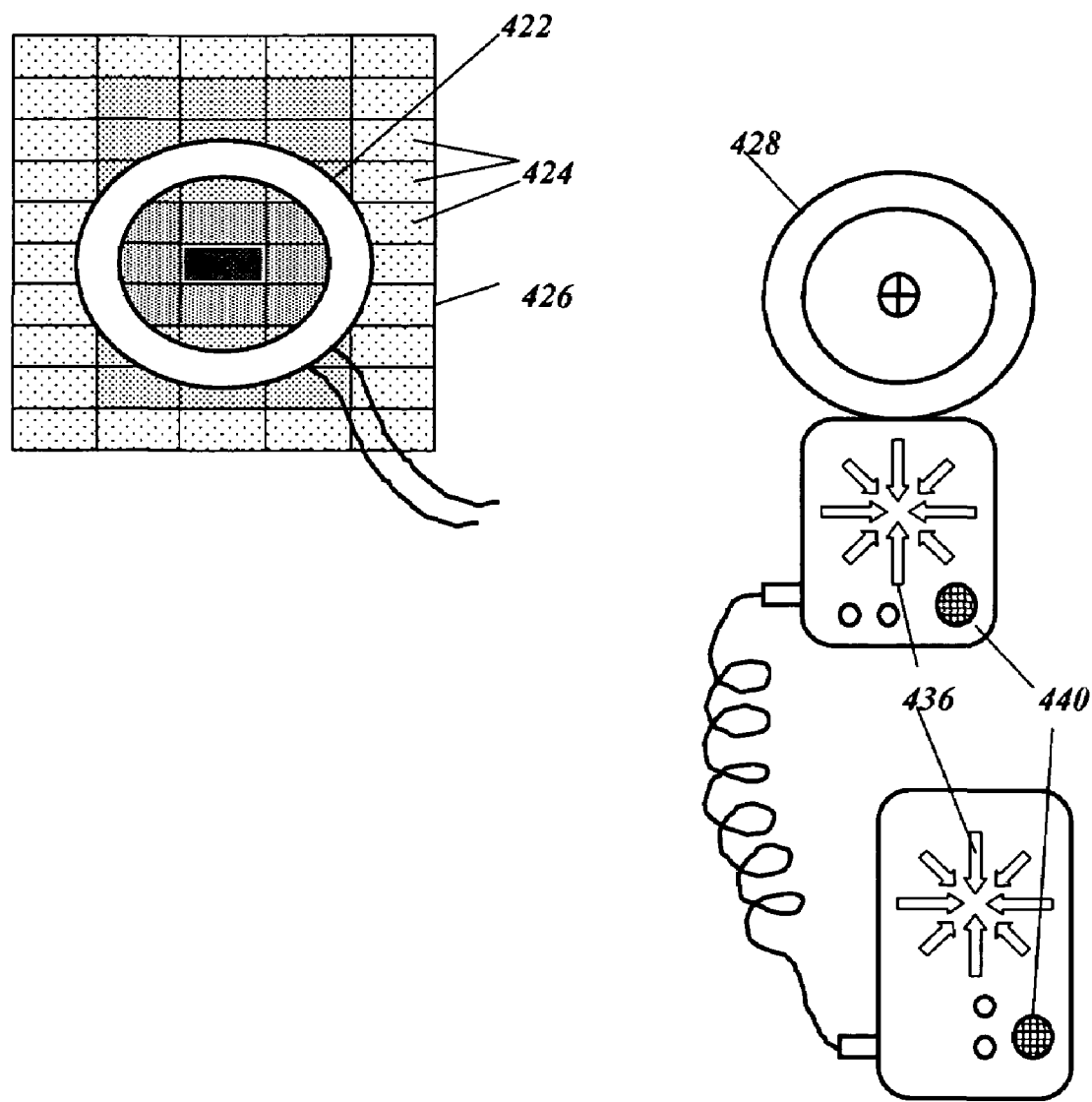
FIG. 8 is a diagram of a microchip array homing device.

FIG. 8 illustrates an alternative approach to precisely locating the secondary charging coil 422. Here, sets of implantable microchips 424 are arranged in certain patterns on a carrier 426 in a plane. The microchips 424 act as transponders and may be active or passive and are encoded with either a general code or a code unique to each chip 424. The encoding would best be carried out prior to implantation, although programmable chips may be remotely programmed or reprogrammed after implantation. In this embodiment, an RF scanner/transceiver 428 is used to scan through the patient's skin. The individual microchips 424 will return the code with which they were programmed. Because the chips are precisely arranged under the secondary coil, the location of the scanner/transceiver 428 relative to the center of the secondary charging coil 422 may be determined and visually displayed 436 or aurally signaled 440 to the user. It may be noted that the secondary charging coil may be located by monitoring the battery charging voltage via a remote communications device. Moving the primary charging coil in the vicinity of the secondary coil will cause fluctuations in the charging voltage depending on the proximity of the two coils. The charging voltage will be maximal when most closely aligned. This approach is effective, but not nearly as precise as the use of a Hall effect sensor or microprocessor/transponder array as described above.

The specific implementations disclosed above are by way of example and for enabling persons skilled in the art to implement the invention only. We have made every effort to describe all the embodiments we have foreseen. There may be embodiments that are unforeseeable and which are insubstantially different. We have further made every effort to describe the invention, including the best mode of practicing it. Any omission of any variation of the invention disclosed is not intended to dedicate such variation to the public, and all unforeseen, insubstantial variations are intended to be covered by the claims appended hereto. Accordingly, the invention is not to be limited except by the appended claims and legal equivalents.

What is claimed is:

1. An implantable power module, comprising:
   a hermetically sealed biocompatible case;
   an electrochemical energy storage device housed in the case;
   a power management circuit housed within the case;
   a couple for remotely communicating with the power module, the couple being in electrical communication with the power management circuit;
   at least one connector for functionally interconnecting the electrochemical energy storage device and an implantable medical device such that the electrochemical energy storage device powers the medical device, and
   excluding electronics for controlling operation of the implantable medical device.

2. The implantable power module of claim 1, wherein the power management circuit includes a data processing circuit.

3. The implantable power module of claim 1, further comprising:
   a homing device for locating the power module after it is implanted.

4. The implantable power module of claim 1, wherein the electrochemical energy storage device includes at least one primary battery.

5. The implantable power module of claim 1, wherein the electrochemical energy storage device includes at least one rechargeable battery.

6. The implantable power module of claim 5, wherein the electrochemical energy storage device also includes at least one primary battery.

7. The implantable power module of claim 1, wherein the electrochemical energy storage device includes at least one capacitor.

8. The implantable power module of claim 1, wherein the at least one connector includes a combined power and data connector.

9. The implantable power module of claim 1, wherein the at least one connector includes at least one power connector, and at least one data connector.

10. The implantable power module of claim 5, wherein the couple includes a secondary inductive coil interoperatively connected to the rechargeable battery wherein a fluctuating electromagnetic field generates a current in the secondary inductive coil effecting recharging of the rechargeable battery.

11. The implantable power module of claim 10, wherein the power management circuit controls the recharging.

12. The implantable power module of claim 10, wherein the secondary inductive coil at least partially surrounds the electrochemical storage device.

13. The implantable power module of claim 5, wherein at least a portion of the rechargeable battery is shielded with a ferrous magnetic material.

14. The implantable power module of claim 13, wherein the a ferrous magnetic material includes ferrite.

15. The implantable power module of claim 5, wherein at least a portion of the power management circuit is shielded with a ferrous magnetic material.

16. The implantable power module of claim 15, wherein the a ferrous magnetic material includes ferrite.

17. The implantable power module of claim 1, wherein the power management circuit manages the safety and operation of the implantable power module.

18. The implantable power module of claim 17, wherein the power management circuit senses and responds to one or more conditions selected from a group consisting of overcharging, over-discharging, excessive battery temperature, abnormal voltage, and abnormal current.

19. The implantable power module of claim 18, wherein responding to one or more conditions includes disconnecting the electrochemical energy storage device from at least one electrical circuit.

20. The implantable power module of claim 1, wherein the hermetically seated biocompatible case includes at least one of the following: metal and ceramic.

21. The implantable power module of claim 20, wherein the metal includes titanium or an alloy of titanium.

22. The implantable power module of claim 1, wherein the medical device is contiguously attached to the power module and wherein the connecting means includes electrical contacts contained within an external hermetic plug.

23. The implantable power module of claim 1, further comprising:
   a means for communicating status remotely.

24. The implantable power module of claim 23, wherein the means for communicating includes signals carried via the couple.

25. The implantable power module of claim 24, wherein the couple includes an inductive coil.

26. The implantable power module of claim 23, wherein the means for communicating includes a radio frequency transmitter and a radio frequency receiver.

27. The implantable power module of claim 23, wherein the means for communicating includes a light wave transmitter and a light wave receiver.

28. The implantable power module of claim 1, further comprising:
   a means for remotely controlling the power module.

29. The implantable power module of claim 28, wherein the means for controlling the power module includes signals carried via the couple.

30. The implantable power module of claim 29, wherein the couple includes an inductive coil.

31. The implantable power module of claim 28, wherein the means for controlling the power module includes a radio frequency transmitter and a radio frequency receiver.

32. The implantable power module of claim 28, wherein the means for controlling the power module includes a light wave transmitter and a light wave receiver.

33. The implantable power module of claim 3, wherein the power management circuit further includes the homing device for locating the power module.

34. The implantable power module of claim 3, wherein the homing device for locating the power module after it is implanted includes magnetic material.

35. The implantable power module of claim 3, wherein the homing device for locating the power module after it is implanted includes at least one passive transponder.

36. The implantable module of claim 35, wherein the at least one passive transponder includes at least one microchip.

37. The implantable power module of claim 3, wherein the homing device for locating the power module after it is implanted includes at least one active transponder.

38. The implantable power module of claim 37, wherein the at least one active transponder includes at least one microchip.

39. The implantable power module of claim 3, wherein the homing device for locating the power module after it is implanted includes at least one radio frequency transmitter.

40. The implantable power module of claim 39, wherein the homing device for locating the power module after it is implanted further includes an initiator circuit responsive to a signal from outside the power module, wherein the initiator circuit switches on the radio frequency transmitter upon receiving the signal from outside the power module.

41. The implantable power module of claim 40, wherein the signal from outside the power module includes a radio frequency signal.

42. The implantable power module of claim 40, wherein the signal from outside the power module includes a magnetic field.

43. The implantable power module of claim 40, wherein the signal from outside the power module includes an audio signal.

44. The implantable power module of claim 40, wherein the signal from outside the power module includes a light signal.

45. The implantable power module of claim 3, wherein the homing device for locating the power module after it is implanted includes a metal object wherein the metal object is detectible transcutaneously with a metal detector.

46. The implantable power module of claim 3, wherein the homing device for locating the power module after it is implanted includes a light-producing device detectable transcutaneously.

47. The implantable power module of claim 46, wherein the light-producing device includes at least on light-emitting diode.

48. The implantable power module of claim 46, wherein the light producing device emits light in the approximately 400 to 700 nm range.

49. The implantable power module of claim 46, wherein the light producing device emits light in the approximately 0.8 to 2.5-µm range.

50. The implantable power module of claim 3, wherein the homing device for locating the power module after it is implanted includes radioactive material which can be detected transcutaneously.

51. The implantable power module of claim 3, wherein the homing device for locating the power module after it is implanted includes a biocompatible tendril or protrusion extending from the secondary charger coil intercutaneously such that it may be detected by touch.

52. The implantable power module of claim 3, wherein the homing device for locating the power module after it is implanted includes a biocompatible tendril or protrusion extending transcutaneously from the secondary charger coil to outside the patient's body.

53. The implantable power module of claim 1, wherein the connector for coupling the electrochemical energy storage device to a medical device is further characterized by being detachably connectable to the medical device.

54. The implantable power module of claim 1, wherein the implantable module is monolithic.

55. The implantable power module recited in claim 1, wherein the couple for remotely communicating with the power module uses sound.

56. The implantable power module of claim 1, wherein the implantable power module consists essentially of;
the hermetically sealed biocompatible case;
the electrochemical energy storage device;
the power management circuit;
the couple; and
the at least one connector.

57. A method for charging an implanted electrical storage device, comprising:
providing a power module comprising an electrochemical storage device, a secondary inductive charging coil, a charger circuit, a protection circuit, a magnetic material, and excluding electronics for controlling operation of an implantable medical device;
positioning the magnetic material coaxially with the charging coil to create the strongest magnetic field in the center of the charging coil;
implanting the power module into a patient;
providing a primary charging coil comprising a primary inductive coil, a Hall effect sensor located in the center of the primary inductive coil, and a feedback device responsively connected to the Hall effect sensor;
bringing the primary charging coil in proximity to the implanted power module;
moving the primary charging coil until the feedback device signals that the primary charging coil is aligned with the secondary charging coil; and
applying a fluctuating current to the primary charging coil to cause a fluctuating field, inducing a current in the secondary charging coil thereby charging the electrochemical storage device.

58. A method for charging an implanted electrical storage device, comprising:
providing a power module comprising an electrochemical storage device, a secondary inductive charging coil, a charger circuit, a protection circuit, at least one transponder microchip, and excluding electronics for controlling operation of an implantable medical device;
positioning the at least one transponder microchip in proximity to the charging coil to locate the center of the secondary charging coil;
implanting the power module into a patient;
providing a primary charging coil comprising a primary inductive coil, an RF scanner/transceiver, and a feedback device responsively connected to the RF scanner/transceiver,
bringing the primary charging coil in proximity to the implanted power module;
moving the primary charging coil until the feedback device signals that the primary charging coil is aligned with the secondary charging coil; and
applying a fluctuating current to the primary charging coil to cause a fluctuating field, inducing a current in the secondary charging coil thereby charging the electrochemical storage device.

59. The method for charging an implanted electrical storage device recited in claim 58, wherein the at least one transponder microchip includes at least one passive transponder.

60. The method for charging an implanted electrical storage device recited in claim 58, wherein the at least one transponder microchip includes at least one active transponder.

61. The method for charging an implanted electrical storage device recited in claim 58, wherein the at least one transponder microchip is encoded prior to being implanted.

62. The method for charging an implanted electrical storage device recited in claim 58, wherein the at least one transponder microchip is encoded remotely after being implanted.

63. The method for charging an implanted electrical storage device recited in claim 58, wherein the at least one transponder microchip is located directly under the secondary charging coil.

64. The method for charging an implanted electrical storage device recited in claim 58, wherein the at least one transponder microchip includes an array wherein each the transponder microchip is uniquely encoded with respect to the other microchips in the array.

* * * * *